United States Patent [19]

Akamatsu et al.

[11] Patent Number: 5,780,056
[45] Date of Patent: Jul. 14, 1998

[54] MICROCAPSULES OF THE MULTI-CORE STRUCTURE CONTAINING NATURAL CAROTENOID

[75] Inventors: Taku Akamatsu; Ryoji Yasue; Kentaro Kiyama; Noboru Hara, all of Tokyo, Japan

[73] Assignee: Lion Corporation, Tokyo, Japan

[21] Appl. No.: 714,266

[22] Filed: Sep. 17, 1996

[30] Foreign Application Priority Data

May 10, 1996 [JP] Japan .................................. 8-141034

[51] Int. Cl.$^6$ ...................................................... A61K 9/20
[52] U.S. Cl. ........................... 424/464; 424/492; 424/489; 424/456
[58] Field of Search ................... 426/93; 424/489, 424/464, 488, 479, 492, 486, 468, 471

[56] References Cited

U.S. PATENT DOCUMENTS

| | | | |
|---|---|---|---|
| 2,756,177 | 7/1956 | Cannalonga et al. | 424/489 |
| 3,886,294 | 5/1975 | Emodi et al. | 426/540 |
| 3,907,983 | 9/1975 | Seth | 510/379 |
| 3,914,430 | 10/1975 | Cannalonga et al. | 424/284 |
| 3,947,596 | 3/1976 | Cannalonga et al. | 424/344 |
| 3,959,472 | 5/1976 | Cannalonga et al. | 424/252 |
| 3,998,753 | 12/1976 | Antoshkiw et al. | 252/312 |
| 4,375,481 | 3/1983 | Kuwabara et al. | 426/93 |
| 4,522,743 | 6/1985 | Horn et al. | 252/311 |
| 5,185,336 | 2/1993 | Caviezel et al. | 514/251 |
| 5,356,636 | 10/1994 | Schneider et al. | 424/489 |
| 5,364,563 | 11/1994 | Cathrein et al. | 252/311 |
| 5,478,569 | 12/1995 | Berneis et al. | 424/456 |
| 5,567,439 | 10/1996 | Myers et al. | 424/486 |
| 5,618,560 | 4/1997 | Bar-Shalom et al. | 424/486 |

FOREIGN PATENT DOCUMENTS

| | | |
|---|---|---|
| 0278284 | 8/1988 | European Pat. Off. |
| 49-7415 | 1/1974 | Japan . |
| 49-110820 | 10/1974 | Japan . |
| 49-126727 | 12/1974 | Japan . |
| 51-41732 | 4/1976 | Japan . |
| 52-84232 | 7/1977 | Japan . |
| 53-37087 | 10/1978 | Japan . |
| 57-195161 | 11/1982 | Japan . |
| 59-122424 | 7/1984 | Japan . |
| 59-137410 | 8/1984 | Japan . |
| 60-102169 | 6/1985 | Japan . |
| 63-196242 | 8/1988 | Japan . |
| 2-51594 | 2/1990 | Japan . |
| 3-66615 | 3/1991 | Japan . |
| 4-312530 | 11/1992 | Japan . |
| 6-65062 | 3/1994 | Japan . |
| 6-254382 | 9/1994 | Japan . |

OTHER PUBLICATIONS

Murakoshi et al. Cancer Research. vol. 52, pp. 6583–6587 (Dec. 1, 1992).

International Encyclopedia of Food and Nutrition, R.A.Morton, Ed., vol. 9, pp. 129–130 (1970).

*Primary Examiner*—Thurman K. Page
*Assistant Examiner*—William E. Benston, Jr.
*Attorney, Agent, or Firm*—Birch, Stewart, Kolasch & Birch, LLP

[57] ABSTRACT

In a microcapsule of the multi-core structure comprising a plurality of particles which are made of a core material comprising natural carotenoid and an edible oil, and a wall which is made of a coating material based on gelatin, the particles have a mean particle size of 0.01–5 μm, the gelatin has a jelly strength of at least 100 blooms, and the microcapsule has a water content of up to 10% by weight. The microcapsule has a strength enough to protect natural carotenoid from oxidation and deterioration for a long time and to withstand tableting pressure.

24 Claims, 1 Drawing Sheet

MICROCAPSULES OF THE MULTI-CORE STRUCTURE CONTAINING NATURAL CAROTENOID

BACKGROUND OF THE INVENTION

1. Field of the Invention

This invention relates to microcapsules of the multi-core structure containing natural carotenoid and their application. More particularly, it relates to microcapsules of multi-core structure containing natural carotenoid having satisfactory physiological activity to the human body, which have a high strength enough to prevent the carotenoid from being oxidized or deteriorated during long-term storage and to be blended in tablets or the like in a stable manner, and are suitable in such applications as additive agents for foods and pharmaceuticals.

2. Prior Art

Natural carotenoid is a fat-soluble polyene pigment which is yellow, orange or red in color and is blended in foods, health-conscious foods and pharmaceuticals for coloring and nutrition enhancement purposes.

In the prior art, carotenoid is blended as such or after processing it into an oil suspension, microcapsules or powder. As compared with the method of blending carotenoid as such or in oil suspension form, the method of blending carotenoid after processing it into microcapsules or powder is advantageous in that carotenoid can be blended in an end product in a stable manner. Such processing of carotenoid is carried out by forming a colloid dispersed carotenoid preparation as disclosed in Japanese Patent Application Kokai (JP-A) No. 66615/1991, using a liquid or powder preparation as disclosed in JP-A 51594/1990, or preparing microcapsules as disclosed in JP-A 254382/1994.

Carotenoid is generally available in natural and synthetic forms. In the recent market, consumers prefer natural carotenoid because of their nature-oriented favor. Inter alia, natural palm oil carotenoid is superior to those of other origins because it contains α, β, and γ-carotene and lycopene and has anti-carcinogenic activity. See Cancer Research, vol. 52, pp. 6583–6587 (1992).

If synthetic β-carotene which is 100% crystal is used as a core material for microcapsules, a wider degree of freedom is available for the core composition, ensuring that highly stable microcapsules are prepared. In contrast, if natural carotenoid containing more than 40% by weight of edible oil is used as a core material for microcapsules, microcapsules have low strength because the core material is liquid. Undesirably, no stable microcapsules are obtained.

On the other hand, gelatin is often used as a coating material to form a wall or membrane or shell in the manufacture of microcapsules. Since gelatin is a good protective colloid agent, it is effective for stabilizing carotenoid when combined with an antioxidant. More particularly, a protective coating of gelatin is well impermeable to oxygen and advantageous especially for natural carotenoid which is sensitive to oxygen. See International Encyclopedia of Food and Nutrition, vol. 9, pp. 129–130 (1970).

However, if a large amount of edible oil is contained for dispersing natural carotenoid, the resulting microcapsules are reduced in strength and the stabilizing effect of gelatin against oxidation as a protective coating is not fully exerted. Natural carotenoid is then vulnerable to oxidation and deterioration.

Low microcapsule strength has another problem. When microcapsules are blended with a vehicle and compressed into tablets, the microcapsules can be broken during tableting, allowing carotenoid to leak out. It is thus difficult to blend carotenoid in tablets in a stable manner.

SUMMARY OF THE INVENTION

Therefore, an object of the present invention is to provide a microcapsule of the multi-core structure containing natural carotenoid having satisfactory physiological activity to the human body, which has a high strength enough to prevent the carotenoid from being oxidized or deteriorated for a long time and to be blended in tablets or the like in a stable manner, and is suitable in such applications as additive agents for foods and pharmaceuticals.

Another object of the present invention is to provide a tablet containing such microcapsules and an additive agent for foods and pharmaceuticals comprising such microcapsules.

Making research works in order to develop high strength microcapsules in which natural carotenoid can be confined in a stable manner even when natural carotenoid is dispersed in a large amount of edible oil, we have found that high strength microcapsules of the multi-core structure containing natural carotenoid can be obtained by limiting the mean particle size of core particles to a specific range, using gelatin having a specific jelly strength as a coating material, and limiting the water content of microcapsules to a specific range.

More specifically, regarding a microcapsule of the multi-core structure comprising a plurality of particles which are made of a core material comprising natural carotenoid and an edible oil, and a wall which is made of a coating material based on gelatin, we have found that when the core particles have a mean particle size of 0.01 to 5 pm, the gelatin has a jelly strength of at least 100 blooms, and the microcapsule has a water content of up to 10% by weight based on the weight of the microcapsule, the microcapsule has a dramatically increased strength which cooperates with the stabilizing effect of gelatin to prevent natural carotenoid in the microcapsule from oxidation and deterioration. Natural carotenoid is thus protected in a stable manner for a long time.

The resulting microcapsules have sufficient strength to withstand tableting pressure and are very useful in that natural carotenoid having anti-carcinogenic and other favorable physiological activities to the human body can be incorporated in tablets in a stable manner. The microcapsules can be advantageously used in various applications as an additive agent for foods and pharmaceuticals.

According to the present invention, there is provided a microcapsule of multi-core structure comprising a plurality of particles which are made of a core material comprising natural carotenoid and an edible oil, and a wall or shell which is made of a coating material based on gelatin. The core particles have a particle size of 0.01 to 5 μm. The gelatin has a jelly strength of at least 100 blooms. The microcapsule has a water content of up to 10% by weight based on the weight of the microcapsule.

In another aspect, the present invention provides a tablet comprising microcapsules; an additive agent for foods comprising microcapsules; and an additive agent for pharmaceuticals comprising microcapsules as set forth above.

BRIEF DESCRIPTION OF THE DRAWINGS

These and further features of the present invention will be apparent with reference to the following description and drawings, wherein.

the only figure.

DETAILED DESCRIPTION OF THE INVENTION

Figure 1:
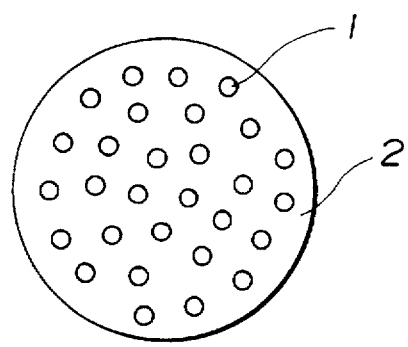
FIG. 1 is a schematic view showing a microcapsule of multi-core structure having natural carotenoid incorporated therein according to the invention.

Microcapsules of the multi-core structure having natural carotenoid incorporated therein according to the invention are comprised of an oil phase component and an aqueous phase component. The oil phase component is a core material comprising natural carotenoid and an edible oil. The aqueous phase component is a coating material based on gelatin having a jelly strength of at least 100 blooms. Particles of the core material are surrounded by a wall or shell of the coating material to give small microcapsules. The water content of the microcapsule is not greater than 10% by weight based on the weight of the microcapsule.

The oil phase component or core material forms a plurality of particles distributed in the coating and contains natural carotenoid, an edible oil and optionally, an antioxidant.

The natural carotenoid which can be used herein includes palm oil carotenoid, donariera algae carotenoid, carrot carotenoid, alfalfa carotenoid, corn carotenoid, and tomato carotenoid alone or in admixture of two or more. It is preferred that at least two carotenoids selected from α-carotene, β-carotene, γ-carotene and lycopene be contained. In this regard, palm oil carotenoid is preferred since it contains α-carotene, β-carotene, γ-carotene and lycopene and has anti-carcinogenic and other favorable physiological activities to the human body.

On use, the carotenoid is suspended in an edible oil. The term oil is used to encompass both oils and fats. The edible oil which can be used herein includes plant oils, animal oils and synthetic oils. Exemplary plant oils are peanut oil, soybean oil, cotton seed oil, and corn oil. Exemplary animal oils are beef tallow, lard, squid oil, and whale oil. Medium chain triglyceride is a typical synthetic oil. These edible oils and fats may be used alone or in admixture of two or more. Carotenoid and edible oil are preferably mixed in a weight ratio between 20/80 and 50/50, more preferably between 25/75 and 40/60. With more amounts of edible oil beyond this range, microcapsules would be fragile. With more amounts of carotenoid beyond this range, the oil phase would have a higher viscosity so that microcapsules might be difficult to handle.

Examples of the antioxidant include ascorbic acid, alkali metal salts of ascorbic acid, tocopherol, esters of gallic acid and ascorbic acid, erysorbic acid, butylated hydroxytoluene (BHT), butylated hydroxyanisole (BHA) alone or in admixture of two or more. Better results are obtained using antioxidants in both the aqueous and oil phases. It is especially preferred to use ascorbic acid in the aqueous phase and tocopherol or ascorbic acid esters in the oil phase. Preferred examples of the ascorbic acid ester are ascorbic palmitate and ascorbic stearate. The antioxidant is blended in an effective amount, typically 0.01 to 15% by weight based on the weight of the microcapsule.

The aqueous phase component which is a coating or wall-forming material of the microcapsules according to the invention is based on gelatin and generally contains conventional amounts of saccharide, antioxidant and stabilizer.

There are generally available a water-soluble gelatin having a jelly strength of 0 bloom (#) and gelation type gelatins having a jelly strength of about 50 blooms (#) to about 400 blooms (#). In the practice of the invention, gelatin should have a jelly strength of at least 100 blooms (#), preferably at least 150 blooms (#). With a jelly strength of less than 100 blooms (#), microcapsules are too fragile to achieve the object of the invention. The gelatin may be of either A or B type. The gelatin having a jelly strength of at least 100 blooms (#) means that when a mixture of two or more gelatins is used, the gelatin mixture has a jelly strength of at least 100 blooms (#). One or more gelatins in the mixture may have a jelly strength of less than 100 blooms (#).

The gelatins may be used alone or in admixture of two or more. When a mixture of two or more gelatins is used, it is advantageous to mix a gelatin having a jelly strength of less than 100 blooms (#) with a gelatin having a jelly strength of at least 300 blooms (#) so as to form a mixture having a jelly strength of at least 100 blooms (#) because the resulting microcapsules are robust. This is advantageous in the manufacture of microcapsules. It is noted that the jelly strength is measured in accordance with JIS K 6503.

The antioxidant used in the aqueous phase component may be the same as those used in the oil phase component although water-soluble ones are preferred. The stabilizer used herein includes citric acid, phosphoric acid, phytic acid, and alkali and alkaline earth metal salts thereof, alone or in admixture of two or more. The stabilizer is used in an effective amount, typically 0.01 to 5% by weight based on the weight of the microcapsule.

Included in the saccharide are monosaccharides, disaccharides, and polysaccharides. Exemplary monosaccharides are arabinoise, xylose, galactose, glucose, mannose, inositol, mannitol, and gluconic acid. Exemplary disaccharides are maltose, agarobiose, isomaltose, saccharose, sophorose, lactose, and stachyose. Exemplary polysaccharides are agarose, amylose, glycomannan, and dextran. These saccharides may be used alone or in admixture of two or more. The saccharide is typically used in an amount of 1 to 30% by weight based on the weight of the microcapsule.

In the microcapsules according to the invention, the aqueous phase component forming the coating or wall is generally used in an amount of 10 to 60% by weight, preferably 20 to 55% by weight based on the weight of the microcapsule.

According to the invention, microcapsules are constructed from the above-mentioned components. Core particles should have a mean particle size of 0.01 to 5 μm, preferably 0.01 to 1 μm. Outside this range, microcapsules are low in strength.

Preferably, microcapsules have a mean particle size of 50 to 3,000 μm, more preferably 100 to 2,000 μm. In microcapsules with a mean particle size of less than 50 μm, the stability of natural carotenoid against oxidation would be insufficient. Microcapsules with a mean particle size of more than 3,000 μm would be poor in outer appearance and difficult to blend with other components for tableting. The ratio of the mean particle size of core particles to the mean particle size of microcapsules should preferably be 1/50 or less, more preferably 1/100 or less. If this ratio is more than 1/50, microcapsules would be low in strength.

According to the invention, the microcapsules should have a water content of up to 10% by weight based on the weight of the microcapsules. The limited water content ensures a microcapsule strength enough to incorporate natural carotenoid in tablets in a stable manner over a long time. Water contents of more than 10% by weight adversely affect microcapsule strength, failing to achieve the objects of the invention. A water content of up to 7% by weight is preferred for suppressing growth of bacteria. The "water content" used herein is measured in accordance with the drying weight loss test method (temperature 105° C., time 1 hour) which is prescribed as a general test method in the food additive regulation. The water content indicates the amount of free water present mainly in the microcapsule wall or coating.

The method of preparing microcapsules according to the invention is not critical. One exemplary method for effectively preparing microcapsules is shown below. In one method, a coating material or wall-forming component is dissolved in water and a core material or oil phase component is emulsified therein to form an O/W type emulsion having a mean oil droplet size of 0.01 to 5 µm. In another preferred method, an W/O type emulsion is first prepared using an oil phase component and a 50 to 80% by weight portion of an aqueous phase component, and the remainder of the aqueous phase component is then added to induce phase inversion emulsification to form an O/W type emulsion having a mean oil droplet size of 0.01 to 1 µm. The emulsifying machine used herein includes an agihomomixer, kneader, and milder, with the agihomomixer being preferred.

In forming microcapsules from the O/W emulsion, a curing-in-liquid or spray cooling technique is often used. The curing-in-liquid technique is to produce microcapsules by curing particles of the O/W emulsion in a dispersing medium such as oils and fats and separating and removing the dispersing medium. More particularly, microcapsules are prepared by dispersing the O/W emulsion in 200 to 1000% by weight of an edible oil at a temperature above the gelling point of gelatin while controlling the dispersing power so that particles may have a mean particle size of 50 to 3,000 µm, cooling the edible oil to a temperature below the gelling point, removing the edible oil as by filtration, and washing the particles with ethyl alcohol or hexane to completely remove the edible oil from the particles.

The spray cooling technique is to produce microcapsules by spraying an O/W emulsion, followed by cooling for solidification and collection. More particularly, microcapsules are prepared by furnishing a tower with an atmosphere set at a temperature below the gelling point of an O/W emulsion and equipped with a rotating disc nozzle or dual fluid pressurizing nozzle, spraying an O/W emulsion at a temperature above the gelling point thereof into the tower through the nozzle so as to form particles having a mean particle size of 50 to 3,000 µm, cooling the particles for solidification, and collecting the particles.

The microcapsules are then dried, for example, by vacuum drying, through flow drying, and fluidized bed drying until the water content of microcapsules is reduced to 10% by weight or less. The drying technique is not critical although it is preferred to dry the microcapsules at a temperature below the gelling point of the O/W emulsion in order to prevent coagulation of microcapsules.

The microcapsules thus obtained according to the invention have the multi-core structure having a core material 1 dispersed in a wall material 2 as shown in FIG. 1.

The microcapsules may be used in any desired application without further processing. Advantageously, microcapsules can be shaped into tablets because they have high strength. Microcapsules are shaped into tablets, for example, by mixing the microcapsules with a vehicle such as lactose, magnesium stearate, corn starch, and saccharide ester and tableting the mixture under a pressure of 200 to 2,000 kg/cm², especially 300 to 1,500 kg/cm². Preferably each tablet contains 0.1 to 30% by weight, especially 1 to 20% by weight of microcapsules.

The microcapsules of the invention are used in a variety of applications as natural carotenoid is conventionally used. In particular, the microcapsules of the invention are used as additives for foods such as health-conscious foods, oil and fat foods, dairy foods, snacks, noodles, seasonings, and fodder and additives for pharmaceuticals such as tablets, capsules and granules.

There have been described microcapsules of the multicore structure containing natural carotenoid. The microcapsules have high strength enough to effectively prevent natural carotenoid from oxidation and deterioration or protect natural carotenoid in a stable manner for a long term and to be tableted without collapse.

Natural carotenoid contained in the microcapsules has favorable physiological activity to the human body and is useful as a naturally occurring pigment. By virtue of these advantages, the microcapsules of the invention are used in a variety of applications, typically in foods and pharmaceuticals.

EXAMPLE

Examples of the present invention are given below by way of illustration and not by way of limitation. All parts are parts by weight (pbw).

Described below are preparation of microcapsules, shaping of microcapsules into tablets, and evaluation of the stability and strength of microcapsules during preparation and tableting.

(1) Preparation of microcapsules (a) Preparation 1 (phase inversion emulsification)

An oil phase was prepared by charging a dissolving tank equipped with an agitator with predetermined amounts of natural carotenoid and edible oil, heating the mixture at 120° C. for dissolution, and then cooling to 70° C. Separately, an aqueous phase was prepared by adding predetermined amounts of gelatin, saccharide and antioxidant to water and heating the mixture at 70° C. for dissolution.

Next, while the oil phase in the dissolving tank was maintained at 70° C., 70% by weight of the aqueous phase was added to the oil phase and thoroughly agitated to form a W/O emulsion. Thereafter, the remainder of the aqueous phase was added to the emulsion to form an O/W emulsion. The O/W emulsion was microencapsulated by a conventional curing-in liquid or spray cooling technique and dried, obtaining microcapsules of the multi-core structure having natural carotenoid incorporated therein.

(b) Preparation 2 (mechanical emulsification)

An oil phase was prepared by charging a dissolving tank equipped with an agitator with predetermined amounts of natural carotenoid and edible oil, heating the mixture at 120° C. for dissolution, and then cooling to 70° C. Separately, an aqueous phase was prepared by adding predetermined amounts of gelatin, saccharide and antioxidant to water and heating the mixture at 70° C. for dissolution.

Next, with stirring at 70° C., the aqueous phase was added to the oil phase in the dissolving tank to form an O/W emulsion. The O/W emulsion was microencapsulated by a conventional curing-in-liquid or spray cooling technique and dried, obtaining microcapsules of the multi-core structure having natural carotenoid incorporated therein. (2) Evaluation of microcapsule stability A bottle with a volume of 1 liter was charged with 10 grams of microcapsules and kept in a constant temperature chamber at 40° C. for 2 months. Thereafter, natural carotenoid left in the microcapsules was extracted with cyclohexane, which was measured for concentration by means of an absorpsiometer. The percent retention of natural carotenoid was calculated from the measured concentration for evaluating the stability of microcapsules.

(3) Evaluation of microcapsule strength

The strength of a microcapsule was determined by means of a Shimazu microcompression tester MCTM-500 by Shimazu Mfg. K.K., by measuring the load under which the particle diameter of a microcapsule was deformed 10%. Compression strength was calculated from the measured load in accordance with the following equation proposed by Hiramatsu et al. (see Journal of the Japanese Mineral Society, vol. 81, No. 10 (1964), 24):

$$St = 2.8P/\pi d^2$$

wherein St is a compression strength (kgf/mm$^2$ or N/mm$^2$), P is a load (kg or N), and d is a particle diameter (mm). Microcapsule strength was evaluated in terms of compression strength.

(4) Evaluation of microcapsules during tableting

A tablet was prepared by blending 445 mg of lactose, 5 mg of magnesium stearate and 50 mg of microcapsules and tableting the blend under a pressure of 1,000 kg/cm$^2$. Whether or not the microcapsules were ruptured was judged immediately after tableting by visually observing whether the tablet was colored red due to oozing of natural carotenoid. The state of microcapsules in a tablet as compacted was evaluated according to the following criterion.

O: no coloring (no microcapsule rupture)

Δ: some coloring (microcapsules were somewhat ruptured)

X: coloring (microcapsules were ruptured)

(5) Evaluation of microcapsule stability in tablet

A bottle with a volume of 1 liter was charged with 20 tablets as prepared in (4) and kept in a constant temperature chamber at 40° C. for 2 months. Thereafter, natural carotenoid left in microcapsules in the tablets was extracted with cyclohexane, which was measured for concentration by means of an absorpsiometer. The percent retention of natural carotenoid was calculated from the measured concentration for evaluating the stability of microcapsules in tablets.

Example 1

Aqueous and oil phases were prepared using gelatin having a jelly strength of 100# (manufactured by Nitta Gelatin K.K.) as an aqueous phase gelatin, saccharose as a saccharide, palm oil carotenoid as carotenoid, corn oil as an edible oil, and tocopherol and ascorbic stearate as an antioxidant as shown in Table 1. using the aqueous and oil phases, microcapsules were prepared by a curing-in-liquid technique in accordance with Preparation 1 (phase inversion emulsification). The microcapsules were subject to stationary vacuum drying at −600 mmHg and 20° C. until a water content of 5% by weight based on the weight of the microcapsules was reached. Microcapsules of the multi-core structure were obtained in this way. Preparation conditions and test results of microcapsules in this Example are shown in Table 1.

Example 2

Microcapsules were prepared by a curing-in-liquid technique as in Example 1 except that gelatin having a jelly strength of 150# was used. The microcapsules were subject to stationary vacuum drying at −600 mmHg and 20° C. until a water content of 5% by weight was reached. Microcapsules of the multi-core structure were obtained in this way. Preparation conditions and test results of microcapsules in this Example are shown in Table 1.

Example 3

Microcapsules were prepared by a curing-in-liquid technique as in Example 1 except that gelatin having a jelly strength of 300# was used and ascorbic palmitate was used instead of ascorbic stearate. The microcapsules were dried in a fluidized bed dryer with air blow at a temperature of 20° C. until a water content of 5% by weight was reached. Microcapsules of the multi-core structure were obtained in this way. Preparation conditions and test results of microcapsules in this Example are shown in Table 1.

Example 4

Microcapsules were prepared by a curing-in-liquid technique as in Example 1 except that gelatin having a jelly strength of 380# was used, palm oil was used instead of corn oil, and ascorbic palmitate was used instead of ascorbic stearate. The microcapsules were dried in a fluidized bed dryer with air blow at a temperature of 2° C. until a water content of 5% by weight was reached. Microcapsules of the multi-core structure were obtained in this way. Preparation conditions and test results of microcapsules in this Example are shown in Table 1.

Example 5

Microcapsules were prepared as in Example 3 except that gelatin having a jelly strength of 300# was used, ascorbic palmitate was used instead of ascorbic stearate, and core particles had a mean particle size of 4.0 μm. Preparation conditions and test results of microcapsules in this Example are shown in Table 1.

Example 6

Microcapsules were prepared by a curing-in-liquid technique as in Example 1 except that there were used a mixture of a gelatin having a jelly strength of 50# and a gelatin having a jelly strength of 300# in a weight ratio of 50/50 (mixture having a jelly strength of 180#) instead of the single 100# gelatin, maltose instead of saccharose, carrot carotenoid instead of palm oil carotenoid, soybean oil instead of corn oil, and ascorbic palmitate instead of ascorbic stearate. The microcapsules were subject to stationary vacuum drying at −400 mmHg and 2° C. until a water content of 7% by weight was reached. Microcapsules of the multi-core structure were obtained in this way. Preparation conditions and test results of microcapsules in this Example are shown in Table 2.

Example 7

Microcapsules were prepared by a curing-in-liquid technique as in Example 1 except that there were used a mixture of a water-soluble gelatin and a gelatin having a jelly strength of 300# in a weight ratio of 20/80 (mixture having a jelly strength of 220#) instead of the single 100# gelatin, glucose instead of saccharose, donariera algae carotenoid instead of palm oil carotenoid, medium chain triglyceride (MCT) instead of corn oil, and ascorbic palmitate instead of ascorbic stearate. The microcapsules were dried in a fluidized bed dryer with air blow at a temperature of 20° C. until a water content of 9% by weight was reached. Microcapsules of the multi-core structure were obtained in this way.

Preparation conditions and test results of microcapsules in this Example are shown in Table 2.

Example 8

Microcapsules were prepared as in Example 1 except that there were used a gelatin having a jelly strength of 300#, ascorbic acid as an aqueous phase antioxidant and a spray cooling technique instead of the curing-in-liquid technique. The microcapsules were dried in a fluidized bed dryer with air blow at a temperature of 20° C. until a water content of 5% by weight was reached. Microcapsules of the multi-core structure were obtained in this way. Preparation conditions and test results of microcapsules in this Example are shown in Table 2.

Example 9

Microcapsules were prepared as in Example 1 except that there were used a gelatin having a jelly strength of 300#, ascorbic acid as an aqueous phase antioxidant, ascorbic palmitate instead of ascorbic stearate and a spray cooling technique instead of the curing-in-liquid technique. The microcapsules were dried in a fluidized bed dryer with air blow at a temperature of 20° C. until a water content of 5% by weight was reached. Microcapsules of the multi-core structure were obtained in this way. Preparation conditions and test results of microcapsules in this Example are shown in Table 2.

COMPARATIVE EXAMPLE 1

Microcapsules were prepared as in Example 3 except that Preparation 2 (mechanical emulsification) was used instead of Preparation 1 and core particles had a mean particle size of 10 μm. Preparation conditions and test results of microcapsules are shown in Table 3.

COMPARATIVE EXAMPLE 2

Microcapsules were prepared as in Example 1 except that a gelatin having a jelly strength of 80# was used. Preparation conditions and test results of microcapsules are shown in Table 3.

COMPARATIVE EXAMPLE 3

Microcapsules were prepared as in Example 1 except that a gelatin having a jelly strength of 50# was used. Preparation conditions and test results of microcapsules are shown in Table 3.

COMPARATIVE EXAMPLE 4

Microcapsules were prepared as in Example 3 except that through flow drying was carried out at a temperature of 20° C. until a water content of 12% by weight was reached. Preparation conditions and test results of microcapsules are shown in Table 3.

COMPARATIVE EXAMPLE 5

Microcapsules were prepared as in Example 3 except that through flow drying was carried out at a temperature of 20° C. until a water content of 15% by weight was reached. Preparation conditions and test results of microcapsules are shown in Table 3.

It is noted in Tables 1 to 3 that with respect to the antioxidant of the oil phase, Toc is tocopherol, As-St is ascorbic stearate, and As-Pt is ascorbic palmitate and that the retention (%) of carotenoid in microcapsules and tablets is after storage at 40° C. for 2 months as mentioned above.

TABLE 1

| | Example | | | | |
|---|---|---|---|---|---|
| | 1 | 2 | 3 | 4 | 5 |
| Aqueous phase | | | | | |
| Gelatin, bloom strength (pbw) | 100# (39) | 150# (39) | 300# (39) | 380# (39) | 300# (39) |
| Antioxidant, type (pbw) | — | — | — | — | — |
| Saccharide, type (pbw) | saccharose (5) | saccharose (5) | saccharose (5) | saccharose (5) | saccharose (5) |
| Water (pbw) | (120) | (120) | (120) | (120) | (120) |
| Oil phase | | | | | |
| Carotenoid, type (pbw) | palm oil (11) | palm oil (11) | palm oil (11) | palm oil (11) | palm oil (11) |
| Edible oil, type (pbw) | corn oil (24) | corn oil (24) | corn oil (24) | palm oil (24) | palm oil (24) |
| Antioxidant, | | | | | |
| type (pbw) | Toc (1) | Toc (1) | Toc (1) | Toc (1) | Toc (1) |
| type (pbw) | As-St (5) | As-St (5) | As-Pt (5) | As-Pt (5) | As-Pt (1) |
| Mean particle size (μm) | | | | | |
| Microcapsule | 420 | 420 | 400 | 400 | 410 |
| Core particle | 0.1 | 0.1 | 0.1 | 0.1 | 4.0 |
| Microcapsule | | | | | |
| Rupture during preparation | ○ | ○ | ○ | ○ | ○ |
| Retention of carotenoid (%) | 96 | 98 | 100 | 100 | 96 |
| Water content (%) | 5 | 5 | 5 | 5 | 5 |
| Strength (kgf/mm²) | 0.63 | 0.65 | 0.72 | 0.75 | 0.63 |
| Tablet | | | | | |
| Microcapsule collapse | ○ | ○ | ○ | ○ | ○ |
| Retention of carotenoid (%) | 90 | 94 | 98 | 99 | 90 |

TABLE 2

| | Example | | | |
|---|---|---|---|---|
| | 6 | 7 | 8 | 9 |
| Aqueous phase | | | | |
| Gelatin*, bloom strength (pbw) | 50#/300# (39) | ws/300# (39) | 300# (39) | 300# (39) |
| Antioxidant, type (pbw) | — | — | ascorbic acid (2) | ascorbic acid (2) |
| Saccharide, type (pbw) | maltose (5) | glucose (5) | saccharose (5) | saccharose (5) |
| Water (pbw) | (120) | (120) | (120) | (120) |
| Oil phase | | | | |
| Carotenoid, type (pbw) | carrot (11) | donariera (11) | palm oil (11) | palm oil (11) |
| Edible oil, type (pbw) | soybean oil (24) | MCT (24) | corn oil (24) | corn oil (24) |
| Antioxidant, | | | | |
| type (pbw) | Toc (1) | Toc (1) | Toc (1) | Toc (1) |
| type (pbw) | As-Pt (5) | As-Pt (5) | As-St (5) | As-Pt (5) |
| Mean particle size (μm) | | | | |
| Microcapsule | 390 | 410 | 410 | 400 |
| Core particle | 0.5 | 1.0 | 0.4 | 0.5 |
| Microcapsule | | | | |
| Rupture during preparation | ○ | ○ | ○ | ○ |
| Retention of carotenoid (%) | 97 | 97 | 100 | 100 |
| Water content (%) | 7 | 9 | 5 | 5 |
| Strength (kgf/mm²) | 0.68 | 0.67 | 0.70 | 0.71 |
| Tablet | | | | |
| Microcapsule collapse | ○ | ○ | ○ | ○ |
| Retention of carotenoid (%) | 95 | 91 | 98 | 98 |

*50#/300# gelatin (50/50 weight ratio) mixture had a jelly strength 180# .
Water soluble gelatin/300# gelatin (20/80 weight ratio) mixture had a jelly strength 220# .

TABLE 3

| | Comparative Example | | | | |
|---|---|---|---|---|---|
| | 1 | 2 | 3 | 4 | 5 |
| Aqueous phase | | | | | |
| Gelatin, bloom strength (pbw) | 300# (39) | 80# (39) | 50# (39) | 300# (39) | 300# (39) |
| Antioxidant, type (pbw) | — | — | — | — | — |
| Saccharide, type (pbw) | saccharose (5) | saccharose (5) | saccharose (5) | saccharose (5) | saccharose (5) |
| Water (pbw) | (120) | (126) | (120) | (120) | (120) |
| Oil phase | | | | | |
| Carotenoid, type (pbw) | palm oil (11) | palm oil (11) | palm oil (11) | palm oil (11) | palm oil (11) |
| Edible oil, type (pbw) | corn oil (24) | corn oil (24) | corn oil (24) | corn oil (24) | corn oil (24) |
| Antioxidant, | | | | | |
| type (pbw) | Toc (1) | Toc (1) | Toc (1) | Toc (1) | Toc (1) |
| type (pbw) | As-Pt (5) | As-Pt (5) | As-Pt (5) | As-Pt (5) | As-Pt (5) |
| Mean particle size (μm) | | | | | |
| Microcapsule | 410 | 420 | 390 | 400 | 400 |
| Core particle | 10 | 0.1 | 0.3 | 0.3 | 0.5 |
| Microcapsule | | | | | |
| Rupture during preparation | Δ | X | Δ | Δ | X |
| Retention of carotenoid (%) | 72 | 30 | 25 | 70 | 46 |
| Water content (%) | 5 | 5 | 5 | 12 | 15 |
| Strength (kgf/mm²) | 0.55 | 0.49 | 0.43 | 0.54 | 0.50 |
| Tablet | | | | | |
| Microcapsule collapse | Δ | X | X | Δ | X |
| Retention of carotenoid (%) | 53 | 15 | 10 | 50 | 20 |

It is evident from Tables 1 to 3 that the microcapsules of COMPARATIVE EXAMPLE 1 were partially ruptured during their preparation since core particles had a too large mean particle size, permitting palm oil carotenoid to deteriorate with the lapse of time. When these microcapsules were blended in tablets, the microcapsules were collapsed because of low strength. It was observed that palm oil carotenoid in the tablets deteriorated with the lapse of time. Also, the microcapsules of COMPARATIVE EXAMPLEs 2 and 3 were fragile since the gelatin having a low jelly strength was used. When the microcapsules of COMPARATIVE EXAMPLES 2 and 3 were blended in tablets, the microcapsules were collapsed, permitting palm oil carotenoid in the tablets to deteriorate to a more extent with the lapse of time than in Comparative Example 1. The microcapsules of COMPARATIVE EXAMPLES 4 and 5 were fragile because of high water contents. When the microcapsules of COMPARATIVE EXAMPLES 4 and 5 were blended in tablets, the microcapsules were collapsed, permitting palm oil carotenoid in the tablets to deteriorate with the lapse of time.

In contrast, the microcapsules of Example 1 avoided rupture during preparation and protected palm oil carotenoid stable for a long term. These microcapsules could be blended in tablets without collapse and were successful in protecting palm oil carotenoid stable for a long term. The microcapsules of Example 2 provided equivalent results to Example 1, with a higher percent retention of carotenoid in tablets than in Example 1. The microcapsules of Example 3 provided equivalent results to Example 1, with a higher percent retention of carotenoid in tablets than in Examples 1 and 2. The microcapsules of Example 4 provided equivalent results to Example 3. The microcapsules of Example 5 showed a little lower percent retention of carotenoid in tablets than in Example 3 because the core particles had a larger mean particle size. The microcapsules of Examples 6 to 9 provided satisfactory results.

Japanese Patent Application No. 141034/1996 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A microcapsule of multi-core structure comprising a plurality of particles which are made of a core material comprising natural carotenoid and an edible oil, and a wall which is made of a coating material based on gelatin, wherein said particles have a mean particle size of 0.01 to 5 µm, said gelatin has a jelly strength of at least 100 blooms, and said microcapsule has a water content of up to 10% by weight based on the weight of said microcapsule.

2. The microcapsule of claim 1 which is microencapsulated by a spray cooling or curing-in-liquid technique.

3. The microcapsule of claim 1 wherein said gelatin has a jelly strength of at least 150 blooms.

4. The microcapsule of claim 1 which has a water content of up to 7% by weight based on the weight of said microcapsule.

5. The microcapsule of claim 1 wherein said particles have a mean particle size of 0.01 to 1 µm.

6. The microcapsule of claim 1 wherein said gelatin has a jelly strength of at least 150 blooms, said microcapsule has a water content of up to 7% by weight based on the weight of said microcapsule, and said particles have a mean particle size of 0.01 to 1 µm.

7. The microcapsule of claim 5 which is microencapsulated by a spray cooling or curing-in-liquid technique.

8. The microcapsule of claim 6 wherein said core material contains natural carotenoid and the edible oil in a weight ratio between 20:80 and 50:50.

9. The microcapsule of claim 6 wherein said particles have a mean core particle size and said microcapsule has a mean microcapsule particle size, the ratio of the core particle size to the microcapsule particle size being up to 1/50.

10. The microcapsule of claim 6 wherein said particles have a mean core particle size and said microcapsule has a mean microcapsule particle size, the ratio of the core particle size to the microcapsule particle size being up to 1/100.

11. The microcapsule of claim 6 which has a mean particle size of 50 to 3,000 µm.

12. The microcapsule of claim 6 which has a mean particle size of 100 to 2,000 µm.

13. The microcapsule of claim 1 which is prepared by a method comprising the steps of forming particles from the core material, microencapsulating the particles with the coating material, and drying the resulting microcapsule.

14. The microcapsule of claim 13 wherein the particle forming step includes phase inversion emulsification.

15. The microcapsule of claim 13 wherein the microencapsulation step includes spray cooling or curing-in-liquid.

16. The microcapsule of claim 13 wherein the drying step includes vacuum drying, through flow drying or fluidized bed drying.

17. The microcapsule as in any one of claims 1 to 16 wherein the natural carotenoid comprises palm oil carotenoid.

18. A tablet comprising microcapsules as set forth in claim 1.

19. An additive agent for foods comprising microcapsules as set forth in claim 1.

20. An additive agent for pharmaceuticals comprising microcapsules as set forth in claim 1.

21. A tablet comprising microcapsules as set forth in claim 1 and a vehicle.

22. The tablet according to claim 21, wherein said vehicle is selected from a group consisting of lactose, magnesium stearate, corn starch and saccharide ester.

23. The tablet according to claim 21, wherein said tablet contains 0.1 to 30% by weight of microcapsules.

24. The tablet according to claim 23, wherein said tablet contains 1 to 20% by weight of microcapsules.

* * * * *